United States Patent [19]

Unhoch et al.

[11] Patent Number: 5,449,658

[45] Date of Patent: Sep. 12, 1995

[54] BIOCIDAL COMPOSITIONS COMPRISING POLYHEXAMETHYLENE BIGUANIDE AND EDTA, AND METHODS FOR TREATING COMMERCIAL AND RECREATIONAL WATER

[75] Inventors: Michael J. Unhoch; Peter S. K. Lee; David G. Chasin, all of Wilmington, Del.

[73] Assignee: Zeneca, Inc., Wilmington, Del.

[21] Appl. No.: 163,448

[22] Filed: Dec. 7, 1993

[51] Int. Cl.$^6$ ............. A01N 47/44; A01N 37/04; A01N 59/14; A01N 59/00

[52] U.S. Cl. ............. 504/151; 504/153; 504/158; 504/159; 424/613; 424/618; 424/630; 424/660; 424/661; 424/719; 424/723; 514/635

[58] Field of Search ............. 504/151, 153, 158, 159; 514/635

[56] References Cited

U.S. PATENT DOCUMENTS

| | | | |
|---|---|---|---|
| 3,874,869 | 4/1975 | Koppensteiner et al. | 71/67 |
| 4,014,676 | 3/1977 | Carter et al. | 71/67 |
| 4,253,971 | 3/1981 | MacLeod et al. | 210/759 |
| 4,537,746 | 8/1985 | Ogunbiyi et al. | 422/28 |
| 4,594,091 | 6/1986 | Girvan | 71/67 |
| 4,758,595 | 7/1988 | Ogunbiyi et al. | 514/635 |
| 4,814,334 | 3/1989 | Salkin | 514/256 |
| 4,836,986 | 6/1989 | Ogunbiyi et al. | 422/28 |

*Primary Examiner*—S. Mark Clardy
*Attorney, Agent, or Firm*—Panitch Schwarze Jacobs & Nadel

[57] ABSTRACT

The growth of algae, fungi and pathogenic organisms in commercial and recreational waters, such as cooling towers, swimming pools and spas, may be controlled by adding to the water a primary sanitizing agent, preferably poly(hexamethylene biguanide) ("PHMB"), and a potentiating adjuvant comprising a calcium ion-chelating agent, preferably ethylenediamine tetraacetic acid ("EDTA"), in amounts such that the adjuvant renders the composition algicidal and fungicidal in water. The water may be further treated with a peroxy salt as a backup agent, preferably sodium perborate, or the calcium ion-chelating agent and peroxy salt may be combined as a shock treatment to water being treated with the primary sanitizing agent.

15 Claims, No Drawings

BIOCIDAL COMPOSITIONS COMPRISING POLYHEXAMETHYLENE BIGUANIDE AND EDTA, AND METHODS FOR TREATING COMMERCIAL AND RECREATIONAL WATER

FIELD OF THE INVENTION

The present invention relates to compositions and methods for treating recreational waters, such as swimming pools and spas, and commercial water, such as cooling towers. More particularly, the invention is directed to compositions and method for controlling the growth of algae, fungi and pathogenic organisms in such waters.

BACKGROUND OF THE INVENTION

The water in swimming pools and spas is constantly recirculated, and fresh water is normally added only to maintain the desired volume. Although the water is usually filtered continuously to keep it free from suspended matter, it is constantly exposed to infection by pathogenic organisms (bacteria), algae and fungi. Treatment is therefore necessary to control these infections and infestations for reasons of hygiene and appearance.

A variety of sanitizing agents or systems have been used for controlling these organisms, including adding to the recreational water about 1–3 ppm chlorine, 3–5 ppm bromine, 0.1–1.0 ppm of copper and/or silver ions, 2–12 ppm alkyl, dialkyl or polymeric quaternary ammonium compounds, or 6–10 ppm poly(hexamethylene biguanide), which is referred to as PHMB. The use of PHMB for controlling algae in swimming pools is described, for example, in U.S. Pat. No. 4,014,676, and PHMB is commercially available from Zeneca Inc. as a chlorine-free swimming pool sanitizer and algistat under the trademark BAQUACIL ®.

However, while PHMB is a good product for killing pathogenic organisms (bactericide) in swimming pools and spas at levels of 6–10 ppm, it is generally only algistatic and fungistatic at these levels. In the swimming pool industry, even with the different sanitizers available, there is still an increase in the number of algae and fungal infestations in pools.

U.S. Pat. No. 4,253,971 of MacLeod et al. describes and claims a method of controlling pathogenic organisms, fungi and algae in water, such as swimming pool water, by using an alkali metal perborate in tablet form as a backup to PHMB to produce an algicidal effect. However, such a product has not been marketed to date, and according to that patent the perborate must be added separately from the PHMB. There is therefore still a need for more effective and more convenient sanitizing products which will have an algicidal and fungicidal effect as well as killing water-borne bacteria.

SUMMARY OF THE INVENTION

The above objects are achieved and the defects of the prior art overcome by the present invention which provides a method for controlling the growth of algae, fungi and pathogenic organisms in recreational water by adding to the water a composition which contains a primary sanitizing agent and a potentiating adjuvant comprising a chelating agent, preferably ethylenediamine tetraacetic acid or a salt thereof (EDTA), in amounts sufficient to render the composition algicidal and fungicidal in water. The primary sanitizing agent may be any of the known bactericides used in pools and the like, including chlorine, bromine, copper and/or silver ions, but is preferably PHMB or a salt thereof. The primary sanitizing agent and chelating agent may be added to the water as a concentrate in aqueous solution, or as granules, tablets or other solid form. Optionally, the water may be further treated with a peroxy salt backup agent.

DETAILED DESCRIPTION OF PREFERRED EMBODIMENTS

While the present invention is applicable to commercial water installations, such as cooling towers and other water systems which are too large to lend themselves readily to sterilization or other means of disinfection, and various types of recreational water systems, such as swimming pools, spas, and the like, the invention will be described below with particular reference to swimming pools and spas, which are the major uses. Similarly, while the present invention may be used to enhance the control of growth of algae, fungi and pathogenic organisms by various primary sanitizing agents, including for example chlorine, bromine, copper and/or silver ions, quaternary ammonium compounds, etc., the invention will be described with particular reference to the enhancement of poly(hexamethylene biguanide) or its salts, individually or collectively referred to as "PHMB."

PHMB is a polymeric biguanide, preferably used as the hydrochloride salt, namely poly(hexamethylene biguanide)hydrochloride, which is commercially available from Zeneca, Inc. under the trademark BAQUACIL ®. PHMB has the advantage that it is completely chlorine-free, has no irritant effect on the eyes, and no objectionable odors or tastes are produced. BAQUACIL ® is generally sold as an aqueous solution containing 20 percent active ingredient (PHMB), which is normally diluted to a pool concentration of at least 6 ppm PHMB, and typically about 6–12 ppm PHMB. However, the preferred concentrations of PHMB in pools, spas, cooling towers, etc. will vary depending upon such factors as climatic conditions, frequency and extent of use of the water, etc.

According to the present invention, it has been found that the biocidal efficacy of PHMB, namely its ability to kill at least the most common types of water-borne bacteria, fungi and algae, may be potentiated by combining the PHMB treatment with a chelating agent, particularly a compound which will chelate calcium ions. Examples of suitable chelating agents include polyphosphates, such as hexametaphosphate or its derivatives; hydroxycarboxylic acids, such as gluconic acid (however, citric acid did not work); aminocarboxylic acids, such as EDTA (ethylenediaminetetraacetic acid) or NTA (nitrilotriacetic acid); amino alcohols, such as TEA (triethanolamine); phosphonic acids, such as hydroxyethylidenediphosphonic acid; and polymeric chelating agents, such as polyethyleneimine.

A particularly preferred chelating agent according to the present invention is ethylenediamine-tetraacetatic acid or a salt thereof, collectively or individually referred to as "EDTA", as a potentiating adjuvant. That is, whereas the usual concentrations of PHMB alone are generally only algistatic and fungistatic, the addition of the EDTA potentiating adjuvant renders the combined treatment algicidal and fungicidal in the water. EDTA is a well known and readily available chemical from a number of sources. Preferably, the EDTA is used in the form of its hydrated tetrasodium salt, which is available from Solvay Interox. EDTA has been used as a "chelating" agent in swimming pools and spas to chelate metals such as iron to prevent staining or scale formation on the walls, particularly of plaster pools. However, EDTA has no fungicidal or algicidal activity of its own, and to our knowledge has not been used as an algistat or fungistat in swimming pools, spas or the like.

The potentiating adjuvant is preferably in a water soluble form, such as a water soluble salt of EDTA, so that it will readily dissolve in the commercial or recreational water, and preferably will also dissolve in the solution of the primary sanitizing agent. Thus, it is most common to provide the primary sanitizing agents to commercial and recreational waters in the form of an aqueous solution in order to allow ready dispersability of the sanitizing agent in the water for treatment purposes. For example, when the primary sanitizing agent is PHMB, the common commercial form of this agent is a 20 percent aqueous solution of PHMB.

In view of the large volumes of water which are treated according to the methods of the present invention, the sanitizing agent and potentiating agent are preferably mixed in concentrated formulations which may be in either liquid or solid form and may vary upon the particular use. In general, liquid concentrates containing about 5–20 weight percent PHMB and about 0.5–10 weight percent EDTA in aqueous solution are preferred. For smaller volume applications such as spas, aqueous formulations containing about 5–10 weight percent PHMB and about 1–10 weight percent EDTA are preferred. For example, using a concentrate containing 10 weight percent PHMB and 3 weight percent EDTA, about 2 ounces of concentrate would be used to treat 150 gallons of spa water. On the other hand, for treating larger volumes of water, such as swimming pools, aqueous formulations containing about 10–20 weight percent PHMB and about 0.5–5 weight percent EDTA are preferred. For example, using a concentrate containing 20 weight percent PHMB and 3 percent EDTA, about 64 ounces of concentrate would be used to treat 10,000 gallons of pool water.

In the case of solid formulations such as granules or tablets, it is preferred to use about 50 to 90 weight percent PHMB and about 10 to 50 weight percent EDTA. Granules of each can be blended together and added to water as quickly dissolving granules, or slower dissolving tablets could be formed by dry-blending EDTA and freeze-dried PHMB and compacting the dry blend into tablets. Using a solid concentrate containing, for example, 90 weight percent PHMB and 10 weight percent EDTA, about 16 ounces of concentrate would be needed to treat 10,000 gallons of pool water.

The product formulations of the present invention can, if desired, include other ingredients useful for treatment of the commercial or recreational water. For example, boric acid or other inorganic acids or acid salts can be added to the formulations in amounts of about 2 to 25 weight percent in order to reduce the pH effect on use. Thus, since EDTA and some other chelating agents have a tendency to raise the pH of the water a couple of tenths, the above acids or acid salts will tend to buffer or decrease the pH to offset the effect of the EDTA.

The compositions of the invention containing PHMB as the primary sanitizing agent and EDTA as the potentiating adjuvant are preferably added to the commercial or recreational water in amounts sufficient to yield a PHMB concentration of about 3 to 14 ppm, and preferably about 6 to 10 ppm in the water, and an EDTA concentration of about 1.5 to 36 ppm, and preferably about 1.5 to 6 ppm in the water.

In general, the composition of PHMB or other primary sanitizing agent and EDTA can be added to the commercial or recreational water at the desired concentration, and only replenished periodically as needed, depending upon the particular use of the water and whether any additional biological load is added to the water over time. Except in cases of particularly heavy use or extra biological loading, it is generally not necessary to add more of the compositions of the invention more frequently than every couple of weeks. On the other hand, if the water to be treated has a particularly high biological load at the start, it may be necessary to add an extra amount of the composition at the start to bring the algae, fungi and pathogenic organisms under control, after which a lower maintenance dose may be used.

The biocidal activity of the PHMB and other primary sanitizing agents may be further enhanced by treating the water with a backup agent comprising a peroxy salt (i.e., a salt which produces hydrogen peroxide in water), such as a percarbonate, peracetate, persulfate, peroxide, or perborate, but preferably with an alkali metal perborate, in a manner similar to that described in U.S. Pat. No. 4,253,971. For example, after an initial treatment of the commercial or recreational water with a PHMB/EDTA composition according to the present invention, the water may be further treated by adding a sodium perborate salt to the water at the rate of about 1 to 36 ppm per week, preferably about 12 to 24 ppm per week as a backup. Sodium perborate is a white crystalline powder which occurs as either the tetrahydrate or monohydrate form. The perborate may be added to the water as a powder, granular or tablet form, as desired.

According to another embodiment of the invention, a tablet or granule containing a chelating agent and a peroxy salt can be used as a shock treatment in addition to the main treatment (sanitizing agent) according to the present invention, in order to challenge and bring under control particularly high infestations of algae, fungi and pathogenic organisms. Such tablets could be provided, for example, in the skimmer of a swimming pool, so that they would dissolve slowly and provide extended treatment during periods of particularly high bather load. For example, a solid formulation for this purpose could contain about 2–10 weight percent chelating agent and about 90–98 percent peroxy compound.

The invention will now be described in more detail with reference to the following specific, non-limiting examples.

TEST EXAMPLE A

Laboratory Screen For Minimum Inhibitory Concentration (MIC)

Inoculum Preparation

A spore/mycelial suspension of Paecilomyces lilacinus was prepared from a pre-plated fungal culture that was two weeks old. The fungal inoculum was made into a suspension with sterile phosphate buffer to approximately $10^6$ colony forming units (cfu)/mL as the test inoculum. One mL of the test inoculum was added per flask for each MIC test set. Each MIC test set was incubated statically at room temperature for a period of two weeks.

MIC Test Set Preparation

The following culture media were made up with 10% Czapek's Dox broth (DIFCO). 100 mL of the prepared culture media was added to each 250 mL Erlenmeyer flask. The MIC test set consisted of five Erlenmeyer flasks plus one flask as a control. The culture media contents of each flask were sterilized under usual autoclave conditions. Each MIC test set was made up of two-fold serial dilutions of the test sample, to be screened for antifungal activity, starting with the highest concentration of test sample used to the lowest concentration tested i.e., 1:1, 1:2, 1:4, 1:8, and 1:16 (dilution ratios). The following were the various concentrations of the selected test samples screened:

| | |
|---|---|
| a. PHME | (16, 8, 4, 2, 1 ppm) |
| b. Tetrasodium ethylenediamine-tetraacetate hydrate (EDTA) | (24, 12, 6, 3, 1.5 ppm) |
| c. Sodium perborate | (48, 24, 12, 6, 3 ppm) |
| d. EDTA plus PHMB at 10 ppm/test flask | (24, 12, 6, 3, 1.5 ppm) |
| e. Sodium perborate plus PHMB at 10 ppm/test flask | (48, 24, 12, 6, 3 ppm) |
| f. EDTA plus sodium perborate at 3 ppm/test flask plus PHMB at 10 ppm/test flask | (24, 12, 6, 3, 1.5 ppm) |
| g. Sodium perborate plus EDTA at 3 ppm/test flask plus PHME at 10 ppm/test flask | (48, 24, 12, 6, 3 ppm) |
| h. Control (no test sample/s added) | (0 ppm) |

Microbiological Analysis

The presence of fungal inhibition was evaluated qualitatively by visual means (presence or absence of visible fungal growth) and quantitatively by standard dilution plate counts (Czapek's Dox Agar Plates) at the end of the two-week incubation period.

Results and Discussion

The results in Table 1 indicate that the three individual test samples of PHMB, EDTA, and sodium perborate showed no inhibitory effect against the test fungi at each of their highest concentrations tested. That is, their MICs were $>16$ ppm, $>24$ ppm and $>48$ ppm, respectively, at the end of the incubation period. This was verified qualitatively where visible fungal growths were present in all of the test flasks similar to that of the control flask with no test sample added. Quantitative evaluation of the control using standard dilution plate counts confirmed the proliferation of the fungi from approximately $10^6$ colony forming units (cfu)/mL at the beginning of incubation to $>10^9$ cfu/mL at the end of the incubation period. The test fungi were not affected by the use of either PHMB, EDTA, or sodium perborate alone at any concentration during the study.

In addition, Table 1 shows that each of the PHMB/EDTA and PHMB/sodium perborate combinations exhibited inhibitory activity against the test microorganism. These combinations had MICs of 3.0 ppm with $<10$ cfu/mL of fungal growth (no visible fungal growth) at the MIC, and were fungicidal at 6.0 ppm concentration with 0.0 cfu/mL fungal plate counts. The PHMB/EDTA combination at a concentration of 1.5 ppm EDTA, had visible fungal growth equal to that of the control flask with standard dilution plate counts of $>10^9$ cfu/mL. Hence, the inhibitory activity of PHMB at 10 ppm concentration against the test microorganism was enhanced by either the presence of EDTA or sodium perborate.

Table 1 further shows the MICs of two additional combinations of PHMB/EDTA/sodium perborate. One combination had the PHMB and sodium perborate levels set at 10 ppm and 3 ppm, respectively, in all the test flasks, while the second combination had the PHMB and EDTA levels set at 10 ppm and 3 ppm, respectively, in all the test flasks. The MICs for the two combinations were found to be $<3.0$ ppm and $<1.5$ ppm, respectively. There was also qualitatively no visible fungal growth and quantitatively $<10$ cfu/mL for both combinations tested. Hence, similar enhancement of the inhibitory effects of PHMB against the test microorganism was observed with three-component combinations of EDTA, sodium perborate, and PHMB at the concentrations tested.

TABLE 1

| | MIC Evaluation Against Pink Fungi/Water Mold | | |
|---|---|---|---|
| TEST SAMPLE | MINIMUM INHIBITORY CONCENTRATION (ppm) | COLONY FORMING UNITS @ MIC cfu/mL | MINIMUM FUNGICIDAL CONCENTRATION (ppm) |
| PHMB | $>16$ | $>10^9$ | $>16$ |
| EDTA | $>24$ | $>10^9$ | $>24$ |
| SODIUM PERBORATE | $>48$ | $>10^9$ | $>48$ |
| PHMB (10 ppm) + EDTA | 3.0 | $<10$ | 6.0 |
| PHMB (10 ppm) + SODIUM PERBORATE | 3.0 | $<10$ | 6.0 |
| EDTA + SODIUM PERBORATE (3 ppm) + PHMB (10 ppm) | $<3.0$ | $<10$ | 6.0 |
| SODIUM PERBORATE + EDTA (3 ppm) + PHMB (10 ppm) | $<1.5$ | $<10$ | $<1.5$ |

CONTROL (no-chemical added)
- initial fungal inoculum size ($1.5 \times 10^6$ cfu/mL)
- final fungal counts after each test run ($>10^9$ cfu/mL)

TEST EXAMPLE B

Tank Trial Recovery/Challenge Studies

Test Tank Set-Up

Each test tank (10 gallon tank) was prepared using 20% aqueous PHMB and synthetic pool water (pH=7.5, total alkalinity=100 ppm, calcium hardness=200ppm). The water temperature was kept ambient, and the PHMB level in the test tank was topped to 8.0 ppm PHMB.

Microbial Challenge

The test tanks were inoculated with prepared fungal inoculum suspension in sterile phosphate buffered water from a pre-plated 2-weeks old fungal stock culture of *Paecilomyces lilacinus* on Czapek's Dox agar. 10 mL of the inoculum at $10^6$ cfu/mL was used to inoculate each test tank, and additional 10 mL fungal inocula were added to the test tanks once a week till the end of the 8-week study.

Bather Load 100 mL of pre-made synthetic bather load, which is composed of key components usually found in perspiration and urine, (5× strength) was added for the first five consecutive days after the test tanks were filled to simulate old swimming pool water condition. Thereafter, 20 mL of bather load at 1× strength was added on a daily basis (Mon–Fri) to each test tank during the rest of the tank trial study to simulate bather load contributions to pool water.

Remedial Treatment

Recovered the fungal challenged test tank using the following combinations of test potentiators (plus PHMB):

| EDTA | 15 ppm at start of test |
| --- | --- |
| Sodium Perborate | 30 ppm/week till end of test |

Chemical/Microbial Sampling and Evaluation

The water in the tanks was monitored each time a microbial test sample was obtained. The water chemistry was analyzed for water balance (pH, total alkalinity, calcium hardness) and PHMB levels. Standard dilution plate counts, using Czapek's Dox agar for fungal counts, were done once a week after microbial sampling. Microbial samples were taken first before the tank was inoculated with fresh inoculum. In addition, the visual presence or absence of fungal growth in each test tank was observed and rated for visible mold on a scale from 0 to 3, where 0=no visible growth, 1=slight visible growth, 2=moderate visible growth, and 3=heavy visible growth. Fungal growth was visually determined as seen on the walls of the tank, the attached semi-submerged styrofoam block, plumbing, and filter element.

Results

The initial fungal plate counts of the tank during the first week of analysis were $4.2 \times 10^5$ cfu/mL with a visible mold count rating of 3. By the second week of treatment, the fungal plate counts were <10 cfu/mL with a visible mold rating of 2. Even with weekly fungal inocula, the fungal plate counts indicated that fungi were not able to proliferate in the presence of the test chemicals (PHMB plus EDTA with sodium perborate backup) by the second week until the end of the 8-week test period.

The visible mold rating was 0 by the third week to the end of the eight week, indicating subsequent control of the sessile fungi growing on the various surface areas of the tank, styrofoam block and filter element. The results obtained confirm the MIC results of Test Example A, indicating the enhanced microbial efficacy of PHMB in the presence of EDTA and sodium perborate at the concentrations tested.

TABLE 2

Tank Trial Evaluation of PHMB + EDTA with Sodium Perborate Backup

| Week | Date | PHMB Levels ppm | pH | Fungal Counts cfu/mL | Visible Mold Rating** |
| --- | --- | --- | --- | --- | --- |
| 1 | 07 APR* | 7.2 | 7.8 | $4.2 \times 10^5$ | 3 |
| 2 | 14 APR | 7.2 | 7.9 | 0 | 2 |
| 3 | 21 APR | 6.8 | 7.8 | 2 | 1 |
|   | 23 APR | — | — | 1 | 0 |
| 4 | 28 APR | 5.8 | 7.9 | 0 | 0 |
|   | 30 APR | — | — | 0 | 0 |
| 5 | 05 MAY | 8.0 | 7.9 | 0 | 0 |
|   | 07 MAY | — | — | 0 | 0 |
| 6 | 12 MAY | 6.4 | 7.8 | 1 | 0 |
|   | 14 MAY | — | — | 0 | 0 |
| 7 | 19 MAY | 6.4 | 7.7 | 0 | 0 |
|   | 21 MAY | — | — | 0 | 0 |
| 8 | 26 MAY | 5.0 | 7.8 | 0 | 0 |
|   | 28 MAY | — | — | 0 | 0 |

*Tank was preinoculated with fixed fungal inoculum for 3 weeks prior to the remediation treatment.
(No PHMB was added to the test tank to allow the growth of fungi before treatment challenge)
**Mold Rating (Visible) 0 to 3
0 - no visible fungal growth on sides of the tank, styrofoam block, and filter element
1 - slight visible fungal growth on sides of tank, styrofoam block, and filter element
2 - moderate visible fungal growth on sides of the tank, styrofoam block, and filter element
3 - heavy visible fungal growth on sides of the tank, styrofoam block, and filter element

TEST EXAMPLE C

Test Pool Studies

Test Pool Set-Up

An outdoor swimming pool having a capacity of 10,000 gallons equipped with a 1 hp recirculating pump and appropriately sized sand filter was treated with an aqueous solution containing PHMB sufficient to yield a pool concentration of 10 ppm PHMB, and 1.25 lb. of EDTA in granular form was added separately to yield a pool concentration of 15 ppm EDTA. One pound of sodium perborate was also added to the pool water on a weekly basis (i.e., 12 ppm per week).

Microbial Challenge

A bacterial inoculum of P. aeruginosa, S. aureus, E. faecalis and E.coli was prepared overnight. The fungal inoculum was prepared from a 3-5 days old fungal culture, and the algal inoculum was prepared from a one week old culture of mustard algae. The test pool was inoculated twice a week with the adjusted number of microorganisms per mL of each different inoculum suspension. The algal inoculum was added only towards the last four weeks of the test pool study.

Bather Load 2 liters of pre-made synthetic bather load (10× strength) was added three times a week to each test pool during the rest of the test pool study to simulate bather load contributions to pool water.

Chemical/Microbial Sampling and Evaluation

The pool water was monitored each time a microbial test sample was obtained. The water chemistry was analyzed for water balance (pH, total alkalinity, calcium hardness) and PHMB levels. Microbial levels were monitored twice a week on consecutive days (i.e., 24 hours apart). Each microbial sampling was done in duplicates per selective media using the membrane filtration method for evaluating total aerobic bacteria, total coliform, fecal coliform, P. aeruginosa, S. aureus, E. faecalis, E. coli, fungal and algal counts.

Results

Table 3 shows that at levels of PHMB between 3–10 ppm the initial addition of 15 ppm of EDTA and weekly additions of 12 ppm of sodium perborate enhanced the antimicrobial efficacy of PHMB. There was no viable microbial growth (bacterial, fungal or algal) for most of the pool water sampled during the 12-week test study.

Viable counts seen for total aerobic bacteria were all <10 cfu/mL with the exception of <50 cfu/mL for one day of sampling, but the counts still passed the EPA set limit of 20,000 total aerobic counts/mL. Viable counts were also seen for Staphylococcus in two test samplings of <10 cfu/mL, but the counts still passed the Zeneca Inc. internal set limit of 500 cfu/mL. There were no viable fungal or algal counts during the 12-weeks study, with the exception of two test samplings with counts of <10 cfu/mL. The overall microbial efficacy of the test combination of PHMB/EDTA/-Sodium Perborate appeared to have adequately controlled the growth of bacterial, fungal and algal species tested for.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

TABLE 3

| Sampling Dates | PHMB Level (ppm) $t=0$; $t=24$ | Total Aerobic Count (CFU/ 100 mL) $t=0$; $t=24$ | Total Coliform (CFU/ 100 mL) $t=0$; $t=24$ | Fecal Coliform (CFU/ 100 mL) $t=0$; $t=24$ | Fecal Streptococcus (CFU/ 100 mL) $t=0$; $t=24$ | *Staphylococcus aureus* (CFU/ 100 mL) $t=0$; $t=24$ | *Pseudomonas aeruginosa* (CFU/ 100 mL) $t=0$; $t=24$ | Fungal Counts (CFU/ 100 mL) $t=0$; $t=24$ | Algal Counts (CFU/ 100 mL) $t=0$; $t=24$ |
|---|---|---|---|---|---|---|---|---|---|
| JULY 06;07 | 6.4;4.4 | 0,2;0,0 | 0,0;0,0 | 0,0;0,0 | 0,0;0,0 | 0,1;0,0 | 0,0;0,0 | 0,0;0,0 | NA;NA |
| JULY 13;14 | 7.6;7.2 | 0,0;0,0 | 0,0;0,0 | 0,0;0,0 | 0,0;0,0 | 0,0;0,0 | 0,0;0,0 | 0,0;0,1 | NA;NA |
| JULY 20;21 | 7.6;7.8 | 0,0; 34,40 | 0,0;0,0 | 0,0;0,0 | 0,0;0,0 | 0,0;0,1 | 0,0;0,0 | 0,0;0,0 | NA;NA |
| JULY 27;28 | 6.8;6.0 | 0,3;0,0 | 0,0;0,0 | 0,0;0,0 | 0,0;0,0 | 0,0;0,0 | 0,0;0,0 | 0,0;0,0 | NA;NA |
| AUG 03;04 | 6.0;6.0 | 0,0;4,6 | 0,0;0,0 | 0,0;0,0 | 0,0;0,0 | 0,0;0,0 | 0,0;0,0 | 0,0;0,0 | NA;NA |
| AUG 10;11 | 6.4;6.4 | 0,3;0,0 | 0,0;0,0 | 0,0;0,0 | 0,0;0,0 | 0,0;0,0 | 0,0;0,0 | 0,0;0,0 | NA;NA |
| AUG 17;18 | 6.8;6.8 | 0,0;0,0 | 0,0;0,0 | 0,0;0,0 | 0,0;0,0 | 0,0;0,0 | 0,0;0,0 | 0,0;0,0 | NA;NA |
| AUG 24;25 | 6.8;6.8 | 0,0;0,0 | 0,0;0,0 | 0,0;0,0 | 0,0;0,0 | 0,0;0,0 | 0,0;0,0 | 0,0;0,0 | NA;0,0 |
| SEPT 02;03 | 6.8;7.2 | 0,0;0,0 | 0,0;0,0 | 0,0;0,0 | 0,0;0,0 | 0,0;0,0 | 0,0;0,0 | 0,0;0,0 | 0,0;0,1 |
| SEPT 07;08 | 6.4;7.2 | 0,3;0,0 | 0,0;0,0 | 0,0;0,0 | 0,0;0,0 | 0,0;0,0 | 0,0;0,0 | 0,0;0,0 | 0,0;0,0 |
| SEPT 14;15 | 7.2;8.6 | 0,0;0,0 | 0,0;0,0 | 0,0;0,0 | 0,0;0,0 | 0,0;0,0 | 0,0;0,0 | 0,0;0,0 | 0,0;0,0 |
| SEPT 21;22 | 6.8;7.6 | 0,0;0,0 | 0,0;0,0 | 0,0;0,0 | 0,0;0,0 | 0,0;0,0 | 0,0;0,0 | 0,0;0,0 | 0,0;0,0 |

We claim:

1. A method for controlling the growth of algae, fungi and pathogenic organisms in commercial and recreational water, comprising adding to the water a composition comprising poly(hexamethylene biguanide) hydrochloride (PHMB) as a primary sanitizing agent and a potentiating adjuvant comprising ethylenediamine-tetraacetic acid or a salt thereof (EDTA) as a calcium ion-chelating agent, in amounts such that the PHMB concentration in the water is about 3 to 14 ppm and the EDTA concentration in the water is about 1.5 to 36 ppm and the adjuvant renders the composition algicidal and fungicidal in the water.

2. A method according to claim 1 wherein said EDTA is tetrasodium ethylenediamine-tetraacetate hydrate.

3. A method according to claim 1 wherein the composition comprises a concentrated aqueous solution containing about 8 to 10 weight percent PHMB and about 1 to 3 weight percent EDTA.

4. A method according to claim 1 wherein the composition is added to the water in an amount to yield concentrations of about 6 to 10 ppm PHMB and about 1.5 to 6 ppm EDTA.

5. A method according to claim 1 wherein the water is further treated with a backup agent comprising a peroxy salt.

6. A method according to claim 5 wherein said peroxy salt is an alkali metal perborate.

7. A method according to claim 6 wherein said backup agent is sodium perborate mono- or tetrahydrate.

8. A method according to claim 6 wherein the backup treatment comprises weekly addition of about 1 to 36 parts salt per million parts water.

9. A concentrate for controlling the growth of algae, fungi, and pathogenic organisms in recreational water, comprising an aqueous solution containing about 5 to 20 weight percent poly(hexamethylene biguanide) or a salt thereof and an amount of ethylenediamine tetraacetic acid or a salt thereof effective for maintaining biocidal utility upon dilution of the composition to a poly(hexamethylene biguanide) concentration of 3–14 ppm.

10. A concentrate according to claim 9 comprising about 8 to 10 weight percent poly(hexamethylene biguanide) hydrochloride and about 0.5 to 10 weight percent tetrasodium ethylenediamine-tetraacetate hydrate.

11. A concentrate according to claim 9 further comprising about 2 to 25 weight percent of an inorganic acid or acid buffering salt.

12. A concentrate according to claim 11 wherein said acid is boric acid.

13. A solid concentrate for controlling the growth of algae, fungi and pathogenic organisms in recreational water, comprising about 50 to 90 weight percent poly(hexamethylene biguanide) or a salt thereof and about 10 to 50 weight percent ethylenediamine-tetraacetic acid or a salt thereof.

14. A shock treatment method for controlling algae, fungi and pathogenic organisms in recreational water being treated with poly(hexamethylene biguanide) hydrochloride (PHMB), comprising adding to the water a concentrate comprising a solid formulation of about 2 to 10 weight percent of ethylenediamine-tetraacetic acid (EDTA) or a salt thereof as a calcium ion-chelating agent and about 90–98 weight percent of a peroxy salt, wherein the EDTA renders the PHMB algicidal and fungicidal and the PHMB concentration in the water is about 3–14 ppm.

15. A method according to claim 14 wherein said peroxy salt is sodium perborate.

* * * * *